United States Patent [19]

Bohn et al.

[11] Patent Number: 4,468,345

[45] Date of Patent: Aug. 28, 1984

[54] PROTEIN (PP$_{17}$), A PROCESS FOR CONCENTRATING AND ISOLATING IT AND ITS USE

[75] Inventors: Hans Bohn, Marburg an der Lahn; Wilhelm Winckler, Wenkbach, both of Fed. Rep. of Germany

[73] Assignee: Behringwerke Aktiengesellschaft, Marburg an der Lahn, Fed. Rep. of Germany

[21] Appl. No.: 518,349

[22] Filed: Jul. 29, 1983

[30] Foreign Application Priority Data

Jul. 30, 1982 [DE] Fed. Rep. of Germany ....... 3228503

[51] Int. Cl.$^3$ .................. C07G 7/00; A61K 35/42; A61K 35/50; A61K 39/395
[52] U.S. Cl. ................. 260/112 R; 260/112 B; 424/85; 424/88; 424/105; 436/543
[58] Field of Search ............ 260/112 R, 112 B; 424/85, 88; 536/543

[56] References Cited

U.S. PATENT DOCUMENTS

| | | |
|---|---|---|
| 4,041,021 | 8/1977 | Bohn ..................... 260/112 R X |
| 4,254,021 | 3/1981 | Bohn et al. ............ 260/112 R X |
| 4,348,316 | 9/1982 | Bohn ..................... 260/112 R |
| 4,368,148 | 1/1983 | Bohn ..................... 260/112 R |
| 4,402,872 | 9/1983 | Bohn ..................... 260/112 R |

*Primary Examiner*—Howard E. Schain
*Attorney, Agent, or Firm*—Finnegan, Henderson, Farabow, Garrett & Dunner

[57] ABSTRACT

The protein PP$_{17}$, which has (a) an electrophoretic mobility in the range between $\beta_1$- and $\alpha_2$-globulins, (b) an isoelectric point of 5.25±0.20, (c) a sedimentation coefficient S$_{20}^o$, w of 2.7±0.1 S, (d) a molecular weight, determined in polyacrylamide gel containing sodium dodecyl sulfate (SDS), of 38,000±2,000, (e) an extinction coefficient E$_{1cm}^{1\%}$ (280 nm) of 8.5±0.4 and (f) a carbohydrate content of 2.1±0.9% containing 0.3±0.2% of mannose, 0.4±0.2% of galactose, 0.2±0.1% of xylose, 1.0±0.3% of N-acetyl-glucosamine and 0.2±0.1% of N-acetyl-neuramin acid, is described.

A process for concentrating and isolating it and its use are also described.

5 Claims, 2 Drawing Figures

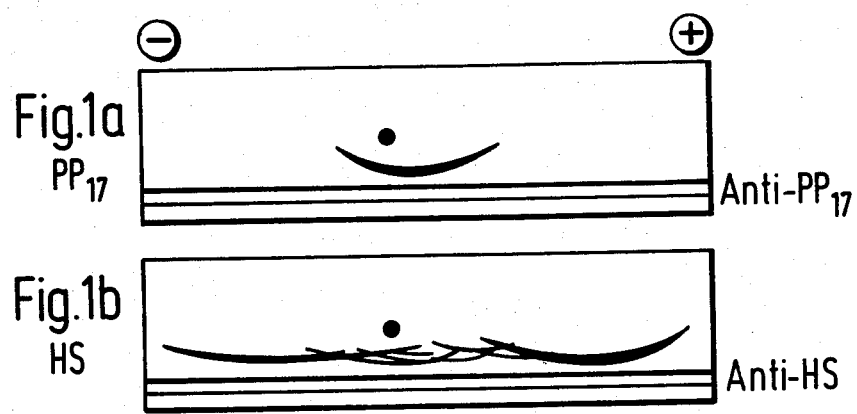

PROTEIN (PP$_{17}$), A PROCESS FOR CONCENTRATING AND ISOLATING IT AND ITS USE

The invention relates to a new protein (PP$_{17}$), a process for concentrating it in and isolating it from the extract of human placentas, and its use.

A number of soluble proteins originating from human placentas have already been detected in the extract from this tissue (Bohn H., Placental and Pregnancy Proteins, in Carcino-Embryonic Proteins, volume I, editor F. G. Lehmann, Elsevier/North-Holland and Biomedical Press, 1979).

The present invention describes the isolation and characterization of a new soluble placenta protein called PP$_{17}$.

On average, 2.5 mg of this protein can be extracted with physiological saline solution from a fully developed human placenta (600 g).

Extracts of other human organs (for example from the heart, lung, skin, stomach, kidney, uterus, liver, spleen, adrenal, colon or bladder) contain only a substantially smaller concentration of this protein or none at all. PP$_{17}$ is usually also absent or present only in traces (<1 mg/liter) in the serum or other body fluids of humans.

The invention relates to the protein PP$_{17}$ which has (a) an electrophoretic mobility in the range between $\beta_1$- and $\alpha_2$-globulins, (b) an isoelectric point of 5.25±0.20, (c) a sedimentation coefficient S$_{20°,w}$ of 2.7±0.1 S, (d) a molecular weight, determined in polyacrylamide gel containing sodium dodecyl sulfate (SDS), of 38,000±2,000, (e) an extinction coefficient E$_{1\,cm}^{1\%}$ (280 nm) of 8.5±0.4 and (f) a carbohydrate content of 2.1±0.9% (0.3±0.2% of mannose, 0.4±0.2% of galactose, 0.2±0.1% of xylose, 1.0±0.3% of N-acetylglucosamine and 0.2±0.1% of N-acetyl-neuramin acid).

The aminoacid composition of PP$_{17}$ is shown in the table below:

| Aminoacid composition of PP$_{17}$ | | |
|---|---|---|
| | Residues per 100 residues (mol %) | Variation coefficient (%) |
| Lysine | 5.86 | 5.52 |
| Histidine | 2.16 | 36.37 |
| Arginine | 5.30 | 2.90 |
| Aspartic acid | 7.44 | 2.59 |
| Threonine | 4.41 | 9.80 |
| Serine | 9.14 | 4.73 |
| Glutamic acid | 18.52 | 2.94 |
| Proline | 4.41 | 5.13 |
| Glycine | 4.93 | 2.92 |
| Alanine | 8.56 | 1.55 |
| Cystine /2 | 0.75 | 3.58 |
| Valine | 6.91 | 3.53 |
| Methionine | 1.46 | 7.89 |
| Isoleucine | 2.53 | 4.70 |
| Leucine | 11.39 | 1.55 |
| Tyrosine | 1.43 | 11.97 |
| Phenylalanine | 2.79 | 7.29 |
| Tryptophan | 1.97 | 8.41 |

The characterizing features of the tissue protein are illustrated by the following statements:

The electrophoretic mobility was investigated by the micromodification with a Microzone R 200 apparatus from Beckman Instruments, on cellulose acetate films (Sartorius) and using sodium diethylbarbiturate buffer of pH 8.6.

The isoelectric point was determined using a column (440 ml) from LKB, Stockholm. The so-called Ampholin ® mixture had a pH range of 4.0 to 6.0 on investigation of the glycoprotein.

The sedimentation coefficient was determined in an analytical ultracentrifuge from Beckman (Spinco apparatus, model E) at 60,000 revolutions per minute in double s-ector cells with the aid of the UV scanner technique at 280 nm. A 0.05M phosphate buffer (pH 6.8) containing 0.2 mole/liter of NaCl was used as the solvent. The protein concentration was adjusted to an optical density of about 3. The sedimentation coefficient was converted on the basis of water at 20° C.

A gel with 7.5% by polyacrylamide (PPA) containing 0.1% of sodium dodecyl sulfate (SDS) was used for determining the molecular weight in the SDS-PPA gel. Human placental lactogen (HPL), human albumin and aggregates thereof were used as the comparison substance.

To determine the extinction coefficient, the substance was dissolved in a concentration of 0.10% (g/100 ml) in distilled water, which had been brought to pH 7.0 by addition of ammonium bicarbonate.

The carbohydrate analysis was carried out as follows: after hydrolysis of the glycosidic bonds, the neutral sugars liberated were separated as borate complexes over an anion exchanger column (Y. C. Lee et al., Anal. Biochem. 27, 567 (1969)), stained in the eluate by admixing Cu-(I) bicinchoninate reagent (K. Mopper and M. Gindler, Anal. Biochem. 56, 440 (1973)) and determined quantitatively using rhamnose as an internal standard. The amino sugars were detected and determined by their reaction with ninhydrin. The neuramin acid content was determined by the method of Warren (Methods in Enzymology, volume VI, 463–465 (1973)).

The aminoacid analysis was carried out by the method of S. Moore, D. H. Spackman and W. H. Stein, Anal. Chem. 30, 1185 (1958), using the liquid chromatograph Multichrom B from Beckman. ½ cystine was determined as cysteic acid after oxidation of the proteins with performic acid (S. Moore et al., Anal. Chem. 30, 1185 (1958)) and subsequent chromatography (S. Moore, J. Biol. Chem. 238, 235 (1963)). The tryptophan content was determined by direct photometric determination by the method of H. Edelhoch, Biochemistry 6, 1948 (1967).

PP$_{17}$ has the following properties, which can be used in a process for its isolation by taking measures corresponding to these properties:

(1) It is precipitated with ammonium sulfate at pH 5–8 and 30–50% saturation from aqueous solutions.

(2) It is precipitated with water-soluble acridine bases, for example 2-ethoxy-6,9-diaminoacridine lactate, at pH values between 7 and 9 and at a concentration of the base of 0.4 to 0.8 g/100 ml and in contrast is not or scarcely precipitated at pH 6.0 if the concentration of the base is ≦0.4 g/100 ml.

(3) On precipitation with ethanol, in dilute salt solutions (for example in 1–2% strength NaCl solution) it remains chiefly in the supernatant liquor at pH 7.0 up to a concentration of 20% by volume of alcohol.

(4) In electrophoretic separation, PP$_{17}$ has a mobility at pH 8.0 between that of $\beta_1$- and $\alpha_2$-globulins.

(5) On isoelectric focusing, it appears in the pH range from 5.1 to 5.4, with a maximum between 5.2 and 5.3.

(6) On dialysis against 0.5M glycine-HCl buffer (pH 2.5), the protein PP$_{17}$ is stable and is not modified immunochemically, in contrast to some other placenta proteins (such as, for example, $PP_9$), which lose their immunochemical reactivity under these conditions.

(7) On gel filtration (Sephadex®), $PP_{17}$ appears in the range of proteins with molecular weights of 20,000 to 60,000.

(8) $PP_{17}$ can be adsorbed onto weakly basic ion exchangers, such as, for example, DEAE-cellulose or DEAE-Sephadex from salt solutions with a low conductivity (about 0–2 mS) and a neutral or weakly alkaline pH value (about pH 7 to 9), and is eluted again from the ion exchanger only when relatively highly concentrated salt solutions (0–2% strength (g/100 ml) NaCl solutions) are used.

(9) $PP_{17}$ can be concentrated in and isolated from its aqueous solution by immunoadsorption.

The invention relates to a process for isolating $PP_{17}$, which comprises fractionating the extract from human placentas using the abovementioned properties.

Besides ammonium sulfate, other neutral salts which are conventionally employed in preparative biochemistry can, of course, also be used for precipitation of the $PP_{17}$. In addition to an acridine base, a water-soluble derivative of a quinoline base, such as those derivatives known for protein fractionations, can also be used in the context of the process according to the invention. According to its electrophoretic properties and its molecular weight, other measures which are suitable for separating off a protein with the given properties from other proteins can also be used to isolate the protein. The various methods of gel filtration, gel chromatography or ultrafiltration or the property $PP_{17}$ has of being able to be bonded to weakly basic ion exchangers from dilute buffer solutions and eluted again with relatively highly concentrated salt solutions can also be used for this purpose.

$PP_{17}$ can be isolated by an appropriate combination of the above measures which effect concentration of $PP_{17}$ or separation of this protein from other proteins.

Accordingly, the present invention relates to the individual steps for concentrating $PP_{17}$ and to the process for the purification of $PP_{17}$ which results by combining the concentration measures.

The example describes the isolation of $PP_{17}$ using the immunoadsorption method. The aqueous extract from human placentas could be used directly for the immunoadsorption. Since the concentration of $PP_{17}$ in the extract is relatively low, it is advantageous first to concentrate specifically the protein $PP_{17}$ by prefractionation of the extract.

The most diverse methods suitable for fractionating proteins on a relatively large scale can in principle be used for this, thus, for example, fractionating precipitation with neutral salts, organic cations or alcohol and separation by gel filtraion or ion exchanger chromatography.

Combined fractionation with water-soluble acridine bases and ammonium sulfate has proved advantageous in many cases in the isolation of placenta proteins. This fractionation has also been used to isolate $PP_{17}$ and is described in the example under (A).

For further concentraion, some of the concomitant proteins were then separated off by precipitation with alcohol.

The concentration steps described in the example are not, however, compulsory and in no way have to be carried out in the sequence described in the example.

The immunoadsorption step could also be replaced by using other separation methods, for example by preparative electrophoresis and isoelectric focusing, after dialysis against an acid buffer of pH 2–4, preferably 0.5M glycine-HCl (pH 2.5).

Gel filtration on Sephadex G-100, ion exchanger chromatography on DEAE-Sephadex and inverse immunoadsorption have proved useful for highly purifying $PP_{17}$.

Besides the parameters mentioned, immunochemical methods can also be used to detect the $PP_{17}$, for example in a fraction from a separation operation, since $PP_{17}$ has antigenic properties. Specific antibodies are formed when animals are immunized with this protein.

An antiserum which can be used for this purpose can be obtained as follows:

On fractionation of the placenta extract with 2-ethoxy-6,9-diaminoacridine lactate and ammonium sulfate by the method of H. Bohn (Arch. Gynäkol. (1971) 210, 440), $PP_{17}$ chiefly passes into placenta fraction III. This fraction is dialyzed against a 0.5M glycine-HCl buffer (pH 2.5) for 14 hours and then neutralized and dialyzed against physiological saline solution. A polyvalent antiserum with which $PP_{17}$ can be detected is obtained by immunizing rabbits with this fraction. This antiserum can be rendered substantially specific against the antigen $PP_{17}$ by absorption with normal human serum and those placenta fractions which do not contain $PP_{17}$. This specific antiserum can be used on the one hand for immunological detection of the $PP_{17}$ and on the other hand for preparation of an immunoadsorbent which can be used for concentrating and isolating $PP_{17}$.

Monospecific antisera can then be prepared directly by immunization of animals by known methods with the aid of the highly purified $PP_{17}$ isolated in accordance with the present application.

FIG. 1a shows the immunological reaction of $PP_{17}$ with a specific antiserum from rabbits after resolution in an electric field in agar-containing gel.

For, comparison, FIG. 1b shows the resolution of the proteins of the serum, rendered visible by their immunoreaction with an antiserum from rabbits against human serum (HS).

The gel diffusion technique according to Ouchterlony (c.f. Schultze and Heremans, Molecular Biology of Human Proteins, volume 1, page 134) or even more sensitive methods, such as radioimmunoassay and enzyme-immunoassay can also be used for immunological detection of $PP_{17}$.

$PP_{17}$ is a more or less placenta-"specific" protein. The detection and determination of such proteins is of diagnostic significance: on the one hand to monitor pregnancies, and on the other hand for the detection of tumors, especially trophoblastic tumors but also non-trophoblastic tumors, and for monitoring the course of a disease and for controlling the therapy of such diseases.

$PP_{17}$ can thus be used to prepare antisera, which can be used for detecting and determining $PP_{17}$.

The invention is illustrated by the example which follows:

EXAMPLE (A) Extraction of the placentas and fractionation of the extract with Rivanol and ammonium sulfate 1,000 kg of deep-frozen human placentas were comminuted in a cutting mixer and extracted with 1,000 liters of 0.4% strength (g/100 ml) sodium chloride solution. After removal of the tissue residue by centrifugation, the extract was then brought to pH 6.0 with 20% strength acetic acid, and 200 liters of a 3% (g/100 ml) solution of 2-ethoxy-6,9-diaminoacridine lactate (Rivanol ®, Hoechst AG) were added, while stirring. The precipitate was centrifuged off and discarded. 1% (g/100 ml) of Betonite A (Erbslöh & Co., Geisenheim/-Rhein) was then added to the supernatant liquor and the mixture was brought to pH 7.0 by addition of 2N NaOH and filtered. 30% (g/100 ml) of ammonium sulfate was slowly added to the filtrate, while stirring; the placenta protein $PP_{17}$ thereby precipitated out, together with other proteins. The precipitate was filtered off; about 12 kg of a moist paste called fraction A in the following text were obtained.

(B) Fractionation with ethanol 500 g of fraction A were dissolved in 400 ml of water and the solution was dialyzed against physiological saline solution at 4° C. After the dialysis, the conductivity of the solution was brought to 15 mS by addition of 5% strength (g/100 ml) NaCl solution. The solution was then cooled to 0° C. and 96% strength ethanol was slowly added, while stirring, until the final concentration of the alcohol was 20% (g/100 ml). The precipitate was removed by centrifugation. The supernatant liquor was dialyzed first against water and then against a 0.1M tris-HCl buffer (pH 8.0) containing 1.0 mole/liter of NaCl and 0.1% (g/100 ml) of $NaN_3$ (buffer solution II). The proteins were then precipitated by addition of 38% (g/100 ml) of solid ammonium sulfate. The precipitate was dissolved in water and the solution was dialyzed against buffer solution II. About 850 ml of a solution (fraction B) containing on average 35 mg of $PP_{17}$ were obtained.

(C) Concentration of $PP_{17}$ by immunoadsorption

1. Preparation of the immunoadsorbent 400 ml of an anti-$PP_{17}$ serum from rabbits were dialyzed against 0.02M phosphate buffer (pH 7.0), and chromatographed on DEAE-cellulose in order to separate off the immunoglobulins. The immunoglobulin fraction (5.95 g of protein) was then reacted with 595 g of specially purified agarose in bead form (Sepharose ® 4 B from Pharmacia, Uppsala, Sweden), which had been activated with 74.4 g of cyanogen bromide, and the immunoglobulin fraction was thus covalently bonded to a carrier.

The process is described by R. Axen, J. Porath and S. Ernbach in Nature 214, 1302 (1967).

With the aid of an immunoadsorbent prepared in this manner, it was possible to isolate the placenta protein $PP_{17}$ from its solution, in particular from placenta fractions enriched with $PP_{17}$.

2. Immunoadsorption procedure

The immunoadsorbent was suspended in buffer solution II (0.1M tris-HCl buffer of pH 8.0, containing 1.0 mole/liter of NaCl and 0.1% of $NaN_3$) and then introduced into a chromatography column (5.0×21 cm) and rinsed with buffer solution II. Half the amount of fraction B was then discharged onto the column, $PP_{17}$ being bonded immunoadsorptively. The column was then rinsed thoroughly with buffer II. Thereafter, the adsorbed protein was eluted from the column with about 600 ml of 3M potassium thiocyanate solution. The $PP_{17}$-containing eluates were dialyzed against buffer solution II and concentrated to about 15 ml in an ultrafilter.

Yield per adsorption: about 6 mg of $PP_{17}$.

Immediately after the elution of $PP_{17}$, the adsorbent in the column was neutralized again and washed thoroughly with buffer solution I; it was then used again for immunoadsorptive bonding of $PP_{17}$.

(D) High purification of $PP_{17}$

The protein obtained by immunoadsorption was frequently still contaminated by serum proteins which were non-specifically bonded and other placenta proteins. Removal of most of the concomitant serum proteins was achieved by gel filtration on Sephadex G-100. The remaining concomitant proteins were then removed by inverse or negative immunoadsorption, i.e. with the aid of carrier-bonded antibodies against the proteins still present as an impurity. These were essentially human placental lactogen (HPL) and immunoglobulins. An erythrocyte protein still present in a small amount in the $PP_{17}$ could finally be removed by chromatography on DEAE-Sephadex. For this, the $PP_{17}$ was discharged and adsorbed onto the column in 0.01M tris-HCl buffer (pH 7.0) and was then eluted by means of a linear salt gradient of 0–2% strength (g/100 ml) NaCl. The erythrocyte protein was thereby adsorbed more firmly on the ion exchanger and eluted from the column only after the $PP_{17}$.

We claim:

1. A protein, $PP_{17}$, extracted from placental tissue, having
   (a) an electrophoretic mobility in the range between $\beta_1$- and $\alpha_2$-globulins;
   (b) an isoelectric point of 5.25±0.20;
   (c) a sedimentation coefficient $S_{20°,w}$ of 2.7±0.1 S;
   (d) a molecular weight, determined in polyacrylamide gel containing sodium dodecyl sulfate (SDS), of 38,000±2,000;
   (e) an extinction coefficient $E_{1\ cm}^{1\%}$ (280 nm) of 8.5±0.4;
   (f) a carbohydrate content of 2.1±0.9% containing 0.3±0.2% of mannose, 0.4±0.2% of galactose, 0.2±0.1% of xylose, 1.0±0.3% of N-acetylglycosamine and 0.2±0.1% of N-acetyl-neuramin acid; and
   (g) an amino acid analysis of

| Amino Acid | Mol % | Variation Coefficient |
|---|---|---|
| Lysine | 5.86 | 5.52 |
| Histidine | 2.16 | 36.37 |
| Arginine | 5.30 | 2.90 |
| Aspartic acid | 7.44 | 2.59 |
| Threonine | 4.41 | 9.80 |
| Serine | 9.14 | 4.73 |
| Glutamic acid | 18.52 | 2.94 |
| Proline | 4.41 | 5.13 |
| Glycine | 4.93 | 2.92 |
| Alanine | 8.56 | 1.55 |
| Cystine /2 | 0.75 | 3.58 |
| Valine | 6.91 | 3.53 |
| Methionine | 1.46 | 7.89 |
| Isoleucine | 2.53 | 4.70 |
| Leucine | 11.39 | 1.55 |
| Tyrosine | 1.43 | 11.97 |
| Phenylalanine | 2.79 | 7.29 |
| Tryptophan | 1.97 | 8.41 |

2. A process for isolating the protein $PP_{17}$ as claimed in claim 1 which comprises subjecting an extract from human placentas containing protein $PP_{17}$ to at least one known procedure for isolating proteins and, in each instance, recovering the material containing the protein to be isolated.

3. The process for concentrating the protein as claimed in claim 1, which comprises subjecting an extract from human placentas to at least one of the following measures and obtaining the $PP_{17}$-enriched fraction:

(1) precipitation with ammonium sulfate in the pH range from 5 to 8 and at 30–50% saturation;

(2) precipitation with a water-soluble acridine base at a pH value between 7 and 9 and a concentration of the base of 0.4–0.8 g/100 ml;

(3) precipitation of concomitant proteins in dilute salt solutions at pH 7.0 up to a concentration of 20% by volume of alcohol;

(4) electrophoretic separation at pH 8.0 and isolation of the fraction with a mobility between that of $\beta_1$- and $\alpha_2$-globulins;

(5) isoelectric focusing in the pH range from 5.1 to 5.4;

(6) dialysis against a buffer solution of pH 2 to 4 and removal of precipitated impurities;

(7) gel filtration to obtain proteins with molecular weights from 20,000 to 60,000;

(8) adsorption onto a weakly basic ion exchanger and elution of the protein; and (9) immunoadsorption.

4. The use of the protein as claimed in claim 1 for obtaining specific antibodies against this protein.

5. The use of the protein as claimed in claim 1 in immunological methods for the detection and determination of this protein.

* * * * *

UNITED STATES PATENT AND TRADEMARK OFFICE
CERTIFICATE OF CORRECTION

PATENT NO. : 4,468,345
DATED : August 28, 1984
INVENTOR(S) : Bohn et al.

It is certified that error appears in the above—identified patent and that said Letters Patent is hereby corrected as shown below:

In the Abstract, line 4, change "$S_{20}°$" to --$S°_{20}$--.

In the Abstract, line 7, change "$E_{1cm}^{1\%}$" to --$E_{1cm}^{1\%}$--.

Claim 1, line 6, change "$S_{20}°$" to --$S°_{20}$--.

Claim 1, line 10, change "$E_{1cm}^{1\%}$" to --$E_{1cm}^{1\%}$--.

Signed and Sealed this

Twelfth Day of February 1985

[SEAL]

Attest:

DONALD J. QUIGG

Attesting Officer     Acting Commissioner of Patents and Trademarks